United States Patent [19]

Lou

[11] Patent Number: 5,328,077
[45] Date of Patent: Jul. 12, 1994

[54] METHOD AND APPARATUS FOR TREATING FEMALE URINARY INCONTINENCE

[76] Inventor: Ek-Seng Lou, 2296 Opitz Blvd., Woodbridge, Va. 22191

[21] Appl. No.: 978,886

[22] Filed: Nov. 19, 1992

[51] Int. Cl.$^5$ .......................................... A61B 17/068
[52] U.S. Cl. ..................................... 227/175; 227/19; 227/107; 227/119; 606/75
[58] Field of Search ................. 227/19, 175, 107, 119, 227/108, 110; 606/72, 75, 142, 143, 219, 148, 150, 139

[56] References Cited

U.S. PATENT DOCUMENTS

| | | |
|---|---|---|
| D. 281,814 | 12/1985 | Pratt et al. |
| D. 284,509 | 7/1986 | Johnson |
| D. 286,442 | 10/1986 | Korthoff et al. |
| 1,179,910 | 4/1916 | Greenfield |
| 1,417,669 | 5/1922 | Langworthy |
| 2,707,783 | 5/1955 | Sullivan ................. 227/19 |
| 4,415,111 | 11/1983 | McHarrie et al. ........... 227/19 |
| 4,438,769 | 3/1984 | Pratt et al. ............... 227/175 |
| 4,454,875 | 6/1984 | Pratt et al. |
| 4,569,469 | 2/1986 | Mongeon et al. ........... 606/75 |
| 4,606,343 | 8/1986 | Conta et al. |
| 4,784,138 | 11/1988 | Kulik et al. |
| 4,873,977 | 10/1989 | Avant et al. |
| 4,887,598 | 12/1989 | Berke |
| 4,979,307 | 12/1990 | Marie |
| 5,040,715 | 8/1991 | Green et al. |
| 5,052,607 | 10/1991 | Dutton ................... 227/119 |
| 5,125,553 | 6/1992 | Oddsen et al. |
| 5,238,167 | 8/1993 | Howard et al. ............ 227/119 |

FOREIGN PATENT DOCUMENTS 218942 7/1924 United Kingdom.
1044633 10/1966 United Kingdom.

*Primary Examiner*—Scott Smith
*Attorney, Agent, or Firm*—Richard C. Litman

[57] ABSTRACT

An improved laparoscopic technique for treating female urinary incontinence and devices for use therein. These devices include an urethral sound, a stapling device, and a staple saw. The sound is substantially L-shaped having a handle at one end and a probe tip at the opposite end. The probe tip has a plurality of beads protruding therefrom which are observable through the wail of the bladder enabling the junction between the lower border of the bladder and urethra to be located. The stapling device attaches the pelvic floor to the pubic bone. The stapling device comprises of a handle, a stapling head, and an elongated member extending therebetween. The stapling head is pivotally attached to the elongated member. A push rod advances a pair of target pins to anchor the pelvic floor to the pubic bone. A small trigger loads staples into a discharge chamber. A large trigger discharges staples from the stapling head into the pelvic floor and pubic bone. The travel of the staple is limited by a stop plate which prevents the staple from being driven through the pelvic floor. In the event the staple is incorrectly discharged, the staple saw is provided for severing the staples and prying the severed staples apart releasing the pelvic floor therefrom. The staple saw is comprised of a handle, a hook for grappling the staple, and an elongated member extending therebetween. A trigger advances a saw blade. A crank manually drives the saw blade.

15 Claims, 10 Drawing Sheets

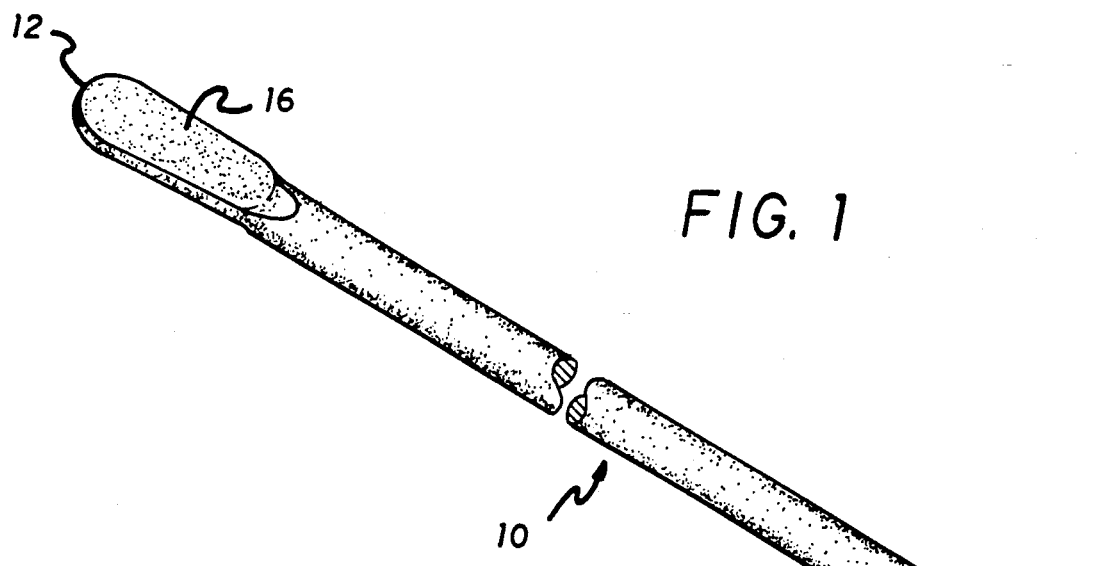
FIG. 1
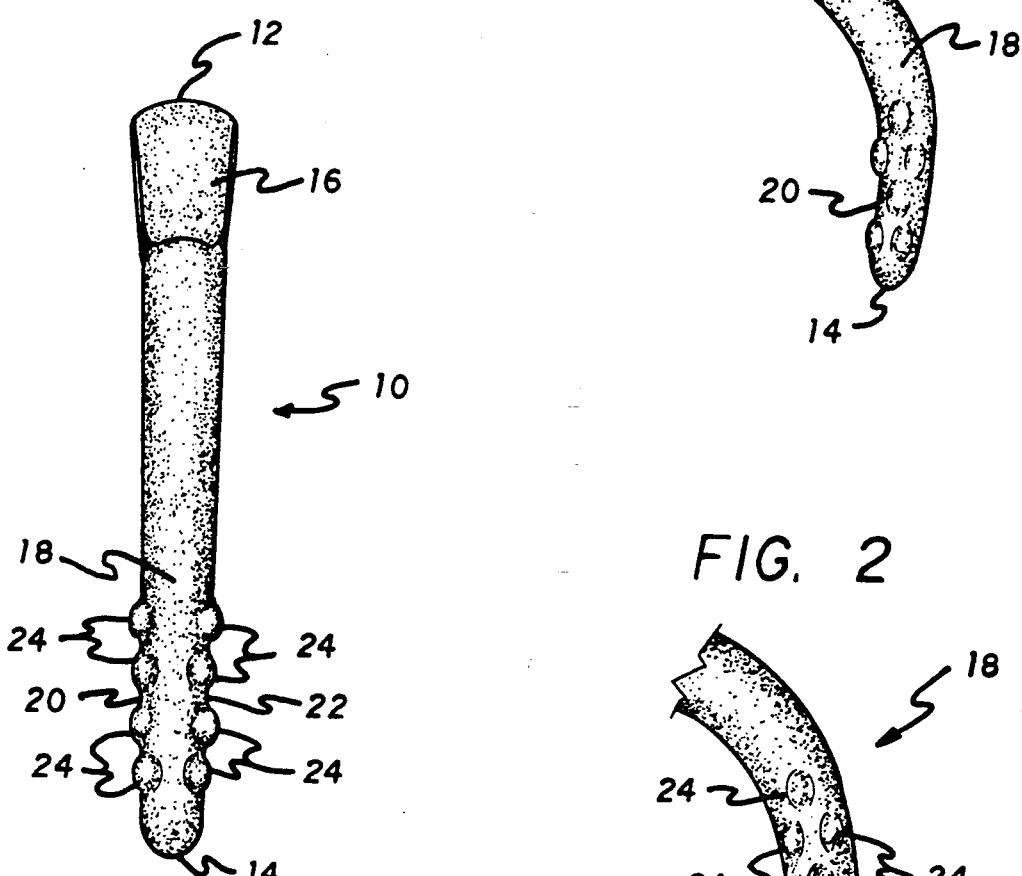
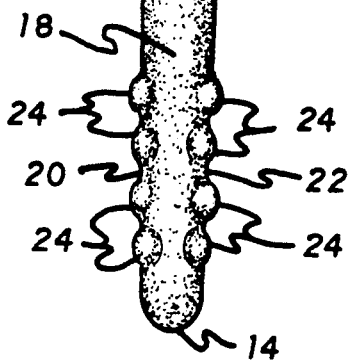
FIG. 3
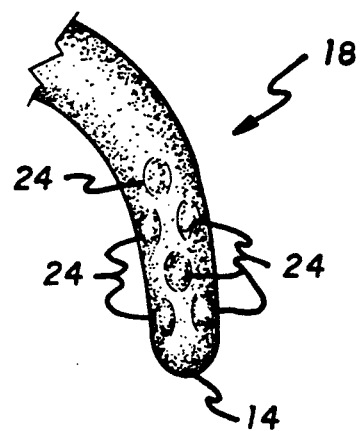
FIG. 2

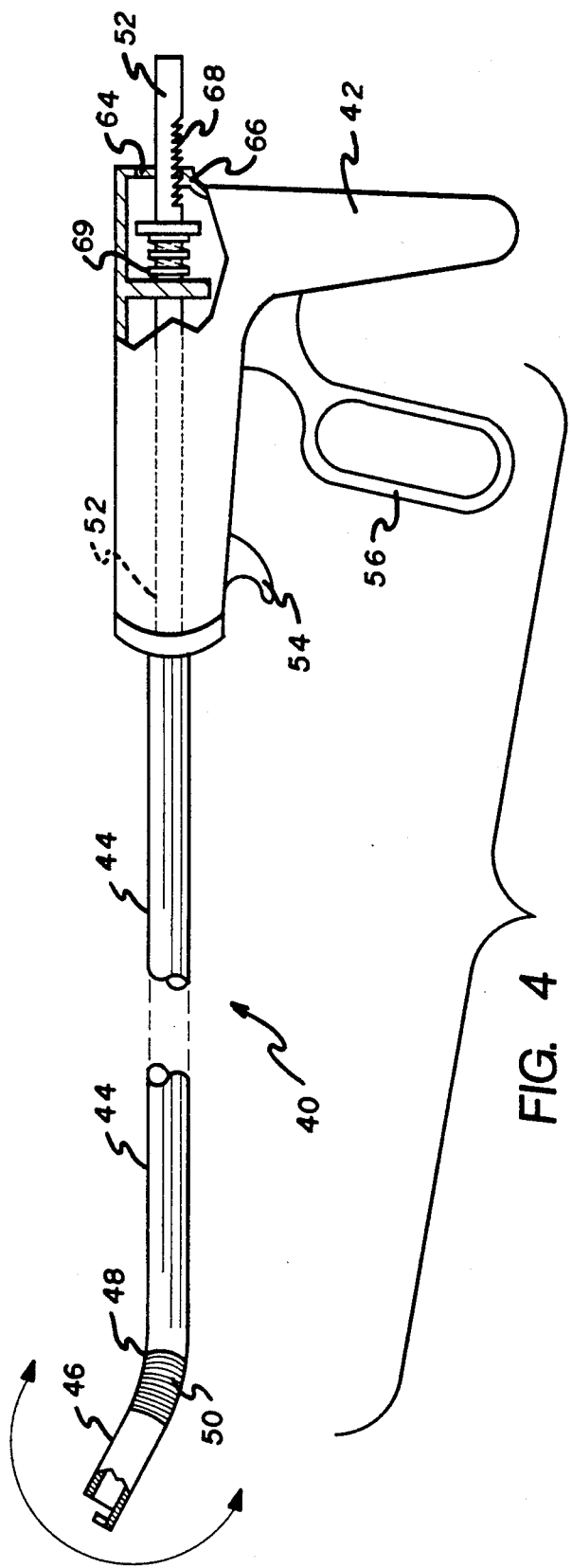
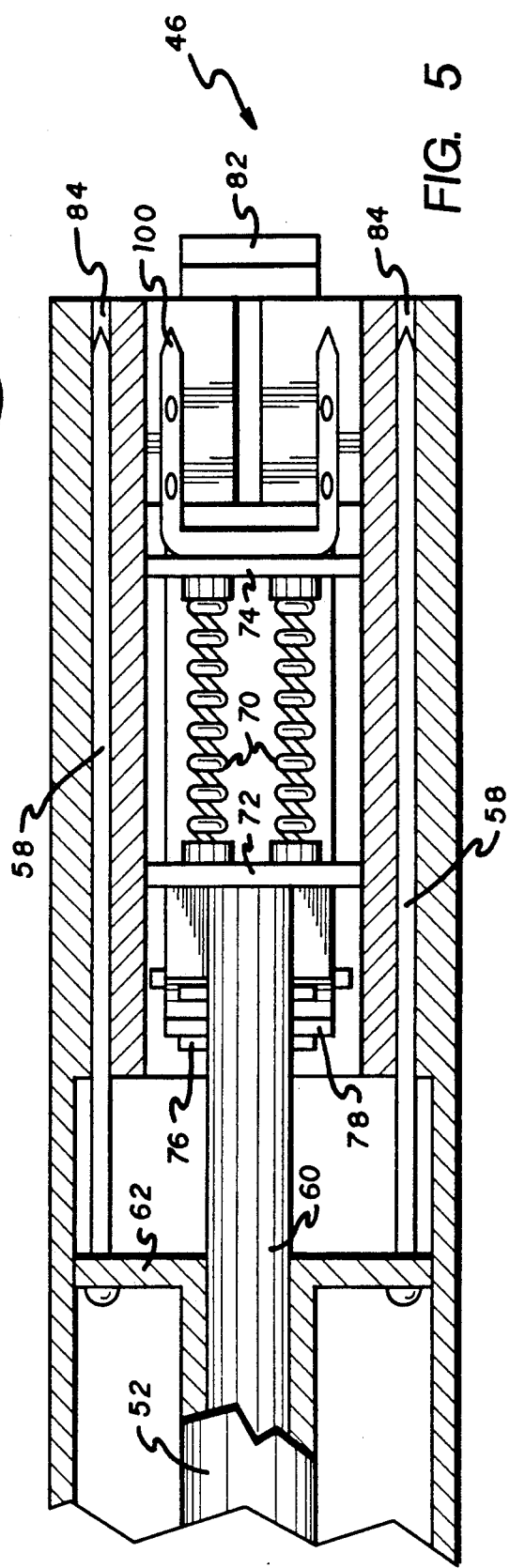
FIG. 4
FIG. 5

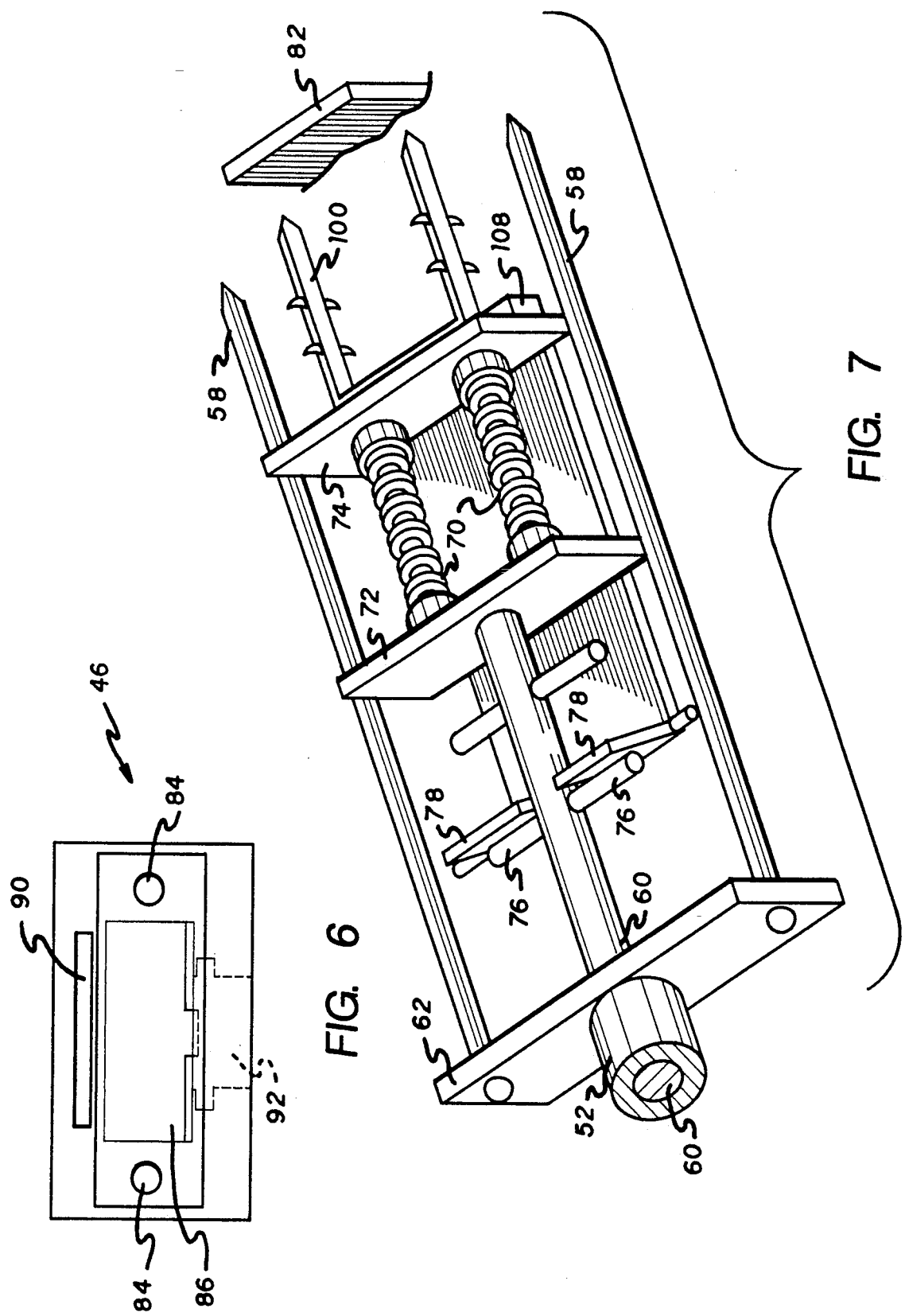

METHOD AND APPARATUS FOR TREATING FEMALE URINARY INCONTINENCE

BACKGROUND OF THE INVENTION

1. Field of the Invention

The present invention relates to devices for use in the treatment of female urinary incontinence and a method of treating female urinary incontinence by lifting the pelvic floor to create a steeper posterior angle between the urethra and the bladder.

2. Description of the Prior Art

To treat female urinary incontinence the pelvic floor is lifted to create a steeper posterior angle between the urethra and bladder. To do this, a surgical technique is used to suspend the pelvic floor from the pubic bone by a suture sling. This surgery is conventionally accomplished by making an incision in the lower abdomen of the patient right above the pubic bone and by approaching the pelvic floor and bladder through the pre vesical space, outside the abdominal cavity. The pelvic floor is sutured to the pubic bone or hung with a suture to the top of the pubic arch.

With the laparoscopic technique; we are able to do the same surgery with staples without having to make traditional open surgical abdominal incisions. This not only reduces the amount of pain experienced by the patient and the length of her hospital stay, it also allows the patient to return to work and other activities much sooner than presently known techniques. The devices used in the laparoscopic technique include an urethral sound, a stapling device, and a staple saw.

One commonly known urethral sound used in urological surgical procedures is, for example, the Van Buren urethra sound manufactured by Dittmar Penn Corporation of the United States. This is an elongated, substantially circumferential, stainless steel sound having a curved end and located opposite the curved end, a flattened end. The curved end is representative of a probe tip and the flattened end is representative of a handle to assist in the manipulation of the urethral sound. Unlike the present invention to be described hereinafter, the Van Buren urethral sound has a smooth surface as opposed to having beads protruding therefrom.

Stapling devices used for suturing are well known in the art. One such stapling device is shown, for example, in Yaroslav P. Kulik U.S. Pat. No. 4,784,137 issued Nov. 15, 1988. Kulik discloses a surgical suturing instrument comprising a handle and a staple jaw extending therefrom. Kulik describes a supporting jaw hingedly attached to the staple jaw permitting the jaw to pivot 180 degrees. The supporting jaw may extend axially or may pivot to a position parallel and juxtaposed to the staple jaw. An alternative stapling device is shown in Odis L. Avant et al. U.S. Pat. No. 4,873,977 issued Oct. 17, 1989. Avant et al. describes a stapling method and apparatus for vesicle-urethral re-anastomosis. The apparatus includes a tubular urethral sound having an inflatable anvil connected thereto. A second implement comprises a connector engagable with the urethral sound. The second implement includes a circular blade for severing a circular opening to allow flow between the bladder and the urethra. A catheter is attached to the anvil and upon the removal of the second implement is closed by a conventional surgical procedure. The anvil upon deflation is withdrawn through the urethra to position the catheter to drain the bladder during the healing of the anastomosis. David T. Green et al. U.S. Pat. No. 5,040,715 issued Aug. 20, 1991 teaches of an apparatus and method of placing staples in laparoscopic and endoscopic procedures. The apparatus places staples and makes incisions. When used in endoscopic procedures, the apparatus includes an anvil member which is mounted to the distal end of an elongated housing. A tubular collar disposed around the arm of the anvil member is movable to bias the anvil member and cartridge assembly into cooperative alignment, thereby clamping the body tissue to be fastened therebetween. Robert G. Oddsen et al. U.S. Pat. No. 5,125,553 issued June 30, 1992 discloses yet another a surgical suturing instrument and method. The surgical instrument staples a hernial opening in internal body tissue. The instrument comprises an elongated staple cartridge rotatably mounted to an elongated frame and an elongated staple forming plate movably mounted to the frame for ejecting a staple from the cartridge into the body tissues and for deforming the staple from an open position to a closed position. This enables the staple to hold together two pieces of body tissue. The instrument further includes a rotator assembly operatively connected to the cartridge for rotating the cartridge.

Surgical staples used in conjunction with stapling devices are also well known in the prior art. One such staple is shown in Clyde R. Pratt et al. U.S. Pat. No. 4,454,875 issued Jun. 19, 1984. Pratt et al shows an osteal medical staple having a cross-bar portion defining gripping surfaces and depending leg portions flaring outwardly a predetermined amount, ensuring that a discrete, constant flaring is obtained once the staple is implanted in the bone. Loosening or reversal of the staple is eliminated by the triangular cross-section of the leg portions. Securing spikes on the under surface of the cross-bar portion are for attaching the soft tissue to the bone. Clyde R. Pratt et al. U.S. Design Pat. No. 281,814 issued Dec. 17, 1985 illustrates a osteal medical staple similar to that shown and described in the above referenced Pratt et al. patent. An alternative surgical staple is shown in Lanny L. Johnson U.S. Design Pat. No. 284,509 issued Jul. 1, 1986. Johnson shows a surgical staple having a cylindrical head and two semi-cylindrical legs. The head includes a centrally disposed threaded bore. The legs flare outwardly.

Also well known in the art are surgical saws. E. J. Greenfield U.S. Pat. No. 1,179,910 issued Apr. 18, 1916 shows, for example, a gear driven surgical saw which is manually driven through wrenching an axially aligned handle. British Patent 218,942 published Jul. 17, 1924 for Allen et al. also shows a gear driven surgical saw. Allen et al., however, teaches of a saw which is manually driven through the rotation of a radially offset wing shaped handle. Another surgical saw is shown in Mitchel Langworthy U.S. Pat. No. 1,417,669 issued May 30, 1922. Langworthy describes a surgical saw which is gear driven by an electric motor.

Other patents which may be of general interest include British Patent No. 1,044,633 published Oct. 5, 1966 for Alexander Ivanovich Boorlakov et al., Herbert W. Korthoff et al. U.S. Design Pat. No. 286,442 issued Oct. 28, 1986, Robert L. Conta et al. U.S. Pat. No. 4,606,343 issued Aug. 19, 1986, Joseph J. Berke, U.S. Pat. No. 4,887,598 issued Dec. 19, 1989, and Ray M. St. Marie U.S. Pat. No. 4,979,307 issued Dec. 25, 1990.

None of the above inventions and patents, taken either singly or in combination, is seen to describe the instant invention as claimed.

SUMMARY OF THE INVENTION

The present invention relates to an improved laparoscopic technique and devices used therein. The technique is directed toward treating female urinary incontinence and the devices used include an urethral sound, a stapling device and a staple saw.

The urethral sound is substantially L-shaped having a handle located at a proximal end and a probe tip disposed at the distal end. The probe tip has opposite sides, each side having a plurality of beads protruding therefrom which can be observed through the wall of the bladder. The sound is purposed for locating the junction between the lower border of the bladder and the urethra.

The stapling device is for stapling the pelvic floor to the pubic bone. The stapling device is comprised of a handle having an elongated member extending therefrom. A stapling head is pivotally attached to a distal end of the elongated member. The handle includes a push rod, a small trigger, and a large trigger. The push rod advances a pair of target pins from the stapling head to gather the pelvic floor and anchor the pelvic floor to the pubic bone. The push rod may be locked into this advanced position through the cooperative engagement of a tooth and one of a plurality of notches. Elongated bores are situated on opposing sides of the stapling head to receive the target pins therethrough and to provide rigid radial support for the same. The small trigger is provided for loading staples into a discharge chamber. The staples are loaded through the use of some conventional staple loading mechanism. The large trigger advances an actuation rod which drives the loaded staple into the pubic bone. The actuation rod advances to compress a pair of coil springs between a compression plate and a drive plate. The compression plate and the drive plate slidably engage opposingly disposed channels to ensure a relative axial alignment. The coil springs join the compression plate and the drive plate to assure that a relative axial motion exists therebetween. The coil springs are compressed to drive the staple into the pubic bone. Further, as the actuation rod advances, a pin passing through the actuation rod engages a leverage plate to leverage a retainer plate clear of the staple thereby releasing the staple from a detained position. A lower cavity offers space for the retainer plate to pivot downward to release the staple. Once released, the staple is driven by the drive plate into the pubic bone anchoring the pelvic floor thereto. The travel of the staple is limited by a stop plate. The stop plate prevents the staple from being driven completely through the pelvic floor.

Staples are stored in and discharged from the upper cavity located within the stapling head. The staples used with the stapling device are substantially U-shaped. The legs of the staple each have opposing surfaces, each surface having one or more barbs which expand slightly after the staple has penetrated into the pubic bone. This slight expansion resists the dislodgement of the staple from the pubic bone.

In the event the pelvic floor is incorrectly stapled to the pubic bone, a staple saw is provided. The staple saw severs the staples into two halves and prying the halves apart to permit the pelvic floor to be removed from the staple. The staple saw is comprised of a handle having an elongate member extending therefrom. The handle is provided with a trigger for advancing a saw blade and a crank for manually driving the saw blade. The elongated member includes a hook opposite the handle. The hook allows the staple being severed to be grappled prior to being cut. To ensure that the staple is completely severed, a crevice is disposed interiorly of the hook to receive the saw blade as the staple is being cut. The saw blade is chain driven which is manually operated by the manual crank. After the staple is cut into two halves, the two halves are pried apart by the hook. With the two halves pried apart, the pelvic floor may be released from the severed staple. Once the pelvic floor is released, the two halves of the staple may be leveraged back together to reduce the risk of internal injury.

The laparoscopic technique is accomplished through the use of the aforementioned devices. The purpose of the technique is to permanently staple the pelvic floor to the pubic bone thereby increasing the posterior angle of the pelvic floor relative to the bladder.

The technique requires the patient to be positioned on a declined surface with her lower body elevated above her upper body. Her abdominal cavity is inflated by carbon dioxide so as to create working space for the surgeon. A trocar is employed for a video camera and one or more working trocar ports are inserted to the abdominal cavity of the patient undergoing the surgical technique. The peritoneal lining at the junction of the pubic bone and the bladder is incised to allow access to the prevesical space.

The fore and index fingers of the surgeon or the surgeon's assistant are inserted into the patient's vagina to tent up the pelvic floor to the desired position for stapling. The urethral sound is inserted through the urethra and into the bladder. The beads on the probe tip of the urethral sound are observable through the bladder wall as the sound is manipulated by the handle. This enables the surgeon to determine the location of the lower border of the bladder, the urethra, and the junction therebetween.

With the urethral sound properly positioned and the fingers tenting up the pelvic floor, the surgeon inserts the stapling device into one of the working trocars and tilts the stapling head at only a slightly tangential angle so as to drive the staple at the proper angle relative to the pubic bone and thus reduce the risk of the staple dislodging therefrom.

The stapling device anchors the pelvic floor to the pubic bone by advancing the target pins forward out of the staple head. With the stapling head positioned correctly, a staple is driven into the pubic bone pinning the pelvic floor to the pubic bone. Once the staple is driven, the stop plate can be removed from behind the staple.

Once the staples are properly in place, the peritoneus lining is reconstituted with conventional staples or sutures. A catheter is inserted into the bladder for drainage of urine and the laparoscopic trocars are removed accordingly.

If a staple is placed in the wrong location, it can be cut into two halves permitting the pelvic floor to be released therefrom. This is accomplished by grappling the staple or sliding the hook under the staple and advancing the saw blade forward against the staple. The crank is rotated thereby driving the saw blade and cutting the staple into two halves. With the staple severed, the hook is used to pry the two halves apart to release the pelvic floor. The two halves are then bent back together to avoid injury to the internal organs.

Accordingly, it is a principle object of the present invention to provide an improved laparoscopic technique for treating female urinary incontinence and devices used therein, such as an improved urethral sound, a stapling device, and a staple saw.

Another object of the present invention is to provide an urethral sound having a handle at one end, a probe tip at an opposite end, and a plurality of beads protruding from the probe tip, the beads being observable through the bladder so as to enable the junction between the lower border of the bladder and the urethra to be established.

Another object of the present invention is to provide a stapling device for stapling the pelvic floor to the pubic bone, the stapling device comprising a pair of target pins for gathering the pelvic floor and anchoring the pelvic floor to the pubic bone, a staple loading mechanism for loading staples into a discharge chamber, and a staple discharging mechanism for discharging staple from the discharge chamber into the pubic bone.

Another object of the present invention is to provide a push rod integral with a push plate for actuating a pair of target pins simultaneously forward and through a pair of bores in a stapling head, extending the target pins a selected distance from the stapling head.

Another object of the present invention is to provide a staple discharging mechanism including an actuation rod for advancing a compression plate to compress a pair of coil springs between the compression plate and a drive plate creating a tension equivalent to that required for driving a staple into the pubic bone and for advancing a leverage plate to pivotally leverage a retainer plate clear of the staple which is discharged so as to release the staple from a detained position.

Another object of the present invention is to provide a stop plate for limiting the travel of the staple being discharged such that the staple is prevented from being driven completely through the pelvic floor.

Yet another object of the present invention is to provide a staple for use with the stapling device, the staple having barbs which expand slightly outwardly to reduce the risk of dislodgement after the staple has penetrated the pubic bone.

It is yet another object of the present invention to provide a staple saw for severing and prying staples apart so as to release the pelvic floor therefrom. The staple saw comprises a hook for grappling the staple being cut, a manually operative circular saw blade for cutting the staple which conforms to the confines of the hook, and a crevice disposed interiorly of the hook for receiving the saw blade as the staple is being cut to ensure that the staple is completely severed.

Another object of the present invention is to provide a laparoscopic technique which is accomplished through the use of the aforementioned devices.

Still another object of the present invention is to provide a laparoscopic technique for reducing the amount of time require for treating female urinary incontinence and for virtually eliminating the need for traditional open surgery.

These and other objects of the present invention will become readily apparent upon further review of the following specification and drawings.

BRIEF DESCRIPTION OF THE DRAWINGS

FIG. 1 is a perspective view of the urethral-bladder sound.

FIG. 2 is a perspective view of the urethral-bladder sound of FIG. 1 taken from the distal end.

FIG. 3 is a side elevational view of the probe tip of the urethral-bladder sound.

FIG. 4 is a partially broken side elevational view of the stapling device.

FIG. 5 is a top view of the stapling mechanism and the target pins.

FIG. 6 is an detail of the stapling head showing the arrangement of the various cavities and bores.

FIG. 7 is a perspective view of the stapling mechanism and the target pins.

Similar reference characters denote corresponding features consistently throughout the attached drawings.

DETAILED DESCRIPTION OF THE PREFERRED EMBODIMENTS

Figure 8:
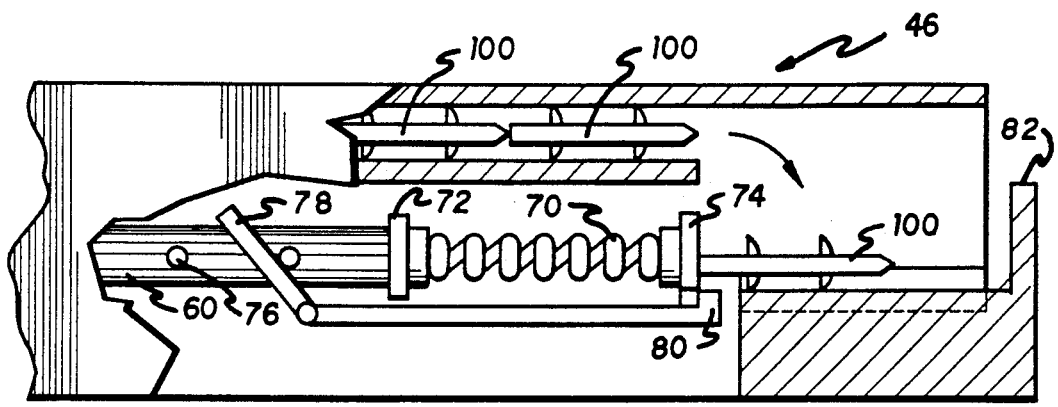
FIG. 8 is a side elevational view of the stapling mechanism relaxed.

The present invention relates to a laparoscopic technique for treating the female urinary incontinence by lifting the pelvic floor PF to create a steeper posterior angle between the urethra U and the bladder B. The laparoscopic technique is accomplished in the usual way using a trocar T1 for a video camera and one or more working trocar ports T2,T3. Other devices used in the laparoscopic technique include an urethral sound 10, a stapling device 40, and possibly, a staple saw 90.

FIG. 1 shows a substantially L-shaped urethral sound 10. The sound 10 is preferably fabricated of a light weight synthetic material coated with silicon or a silicon based substance to facilitate passage of the sound 10 into the urethra U and to avoid traumatic injury to the urethra U. The urethral sound 10 has a proximal end 12 and a distal end 14. The overall length of the urethral sound 10 extending from the proximal end 12 to the distal end 14 is approximately 28 cm. The circumference of the sound 10 ranges from 26 mm to 28 mm. These dimensions are crucial so as to enable the sound 10 to be inserted into the urethra U and allow leverage for manual manipulation. A handle 16 is located at the proximal end 12 of the urethral sound 10 and a probe tip 18 is disposed at the distal end 14. As shown in FIGS. 2 and 3, the probe tip 18 has opposite sides 20,22, each side 20,22 having a plurality of beads 24 protruding therefrom. Each bead 24 is substantially oval having dimensions in the order of 2 mm by 3 mm by 2 mm. Beads 24 of this size can easily seen protruding through the wall W of the bladder B, thus providing an indication of the orientation of the sound 10 during the manipulation of thereof within the bladder B.

FIG. 4 shows a stapling device 40 for stapling the pelvic floor PF to the pubic bone PB. The stapling device 40 is comprised of a handle 42 having an elongated member 44 extending therefrom. A stapling head 46 is pivotally attached to the distal end 48 of the elongated member 44 through some conventional pivotal arrangement 50. This pivotal arrangement 50 enables the stapling head 46 to be axially aligned with the elongated member 44 to permit the insertion of the stapling head 46 into the trocar T2 and once inserted into the trocar T2, the pivotal arrangement 50 further allows the stapling head 46 to be adjusted to a desired angle relative to the elongated member 44. The diameter of the elongate member 44 ranges from 10 to 11 mm to yield to the inside diameter of the trocar T2. The stapling head 46 is preferably 3 to 4 cm in length to accommodate the movement the staple mechanism contained therein. The handle 42 includes a push rod 52, a small trigger 54, and a large trigger 56. The push rod 52 advances a pair of sharp anchor points or target pins 58 (shown in FIGS. 5-10) from the stapling head 46. The small trigger 54 is provided for loading staples 100 (shown in FIGS. 8-10) into the stapling head 46. The loading of the staples 100 into the stapling head 46 is accomplished through the employment of a conventional staple loading mechanism such as that used, for example, in the Endo Clip ML manufactured by Auto Suture of the United States. The large trigger 56 advances an actuation rod 60 (shown in FIGS. 5-10) which drives the staple 100 into the pubic bone PB.

Now, referring to FIGS. 5-7, the push rod 52 extends from the proximal end of the handle 42 toward the distal end 48 and is joined perpendicularly to a push plate 62 having extended from an opposite side thereof the pair of target pins 58. The target pins 58 are extended from the stapling head 46 to gather the pelvic floor PF and anchor the pelvic floor PF to the pubic bone PB. The extending of the target pins 58 is accomplished through the actuation of the push rod 52. As shown in FIG. 4, the push rod 52 enters the handle 42 through an aperture 64 and may be selectively locked into a desired length of extension through the cooperative engagement of a tooth 66 and one of a plurality of longitudinally disposed notches 68. The tooth 66 is disposed interiorly of the aperture 64 and the notches 68 are located along the bottom surface of the push rod 52. The push rod 52 is retracted by a coil spring 69 by applying an upward pressure on the push rod 52 to disengage the tooth 66 from the respective notch 68, in turn, retracting the target pins 58 back into the stapling head 46. The large trigger 56 (shown in FIG. 4) advances the actuating rod 60 in a conventionally known manner to compress a pair of coil springs 70, each coil spring 70 being equal in length and being positioned between a compression plate 72 and a drive plate 74. The coil springs 70 are compressible to a tension equivalent to that needed to drive the staple 100 into the pubic bone PB. As the actuation rod 60 advances, a pin 76 passing through the actuation rod 60 engages a leverage plate 78 to leverage a retainer plate 80 to release the staple 100 from a detained posture. Once released, the staple 100 is driven by the compressed springs 72 into the pubic bone PB anchoring the pelvic floor PF thereto. A stop plate 82 limits the travel of the staple 100 and the depth of penetration of the staple 100 into the pubic bone PB.

As shown in FIGS. 5 and 6, elongated bores 84 are situated on opposing sides of the stapling head 46. The elongated bores 84 permit the passage of the target pins 58 therethrough and provide rigid radial support for the same. The compression plate 72 and the drive plate 74 slidably engage opposingly disposed channels 86 to ensure a relative axial alignment. Further, each coil spring 70 is fixed to one end of the compression plate 72 and to an opposite end to the drive plate 74. The two springs 70 are arranged on opposite sides of and spaced equidistantly apart from the central axis. This spring arrangement assures that a relative axial motion exists between the compression plate 72 and the drive plate 74. FIG. 6 shows an upper cavity 90 and a lower cavity 92. Staples 100 are stored in and discharged from the upper cavity 90. The lower cavity 92 offers space for the retainer plate 80 when the retainer plate 80 pivots downward to release the staple 100.

Figure 9:
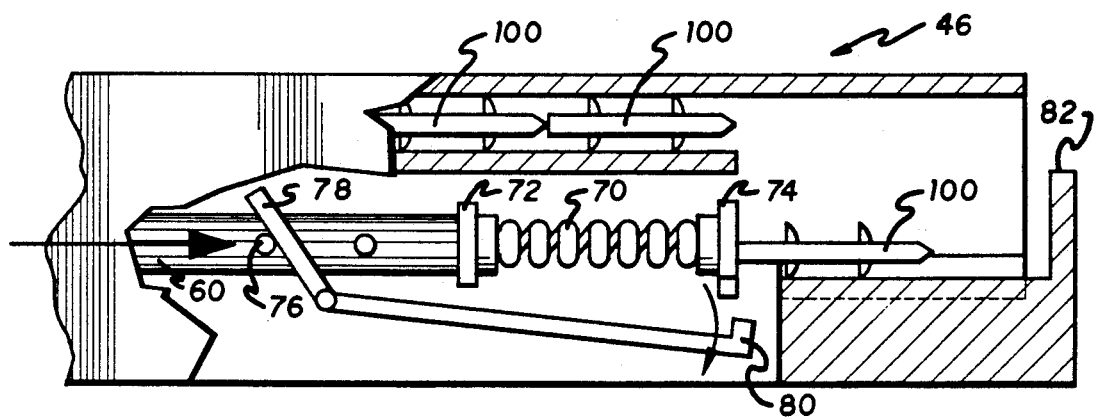
FIG. 9 is a side elevational view of the stapling mechanism with the ejection spring compressed prior to the ejection of the staple.
Figure 10:
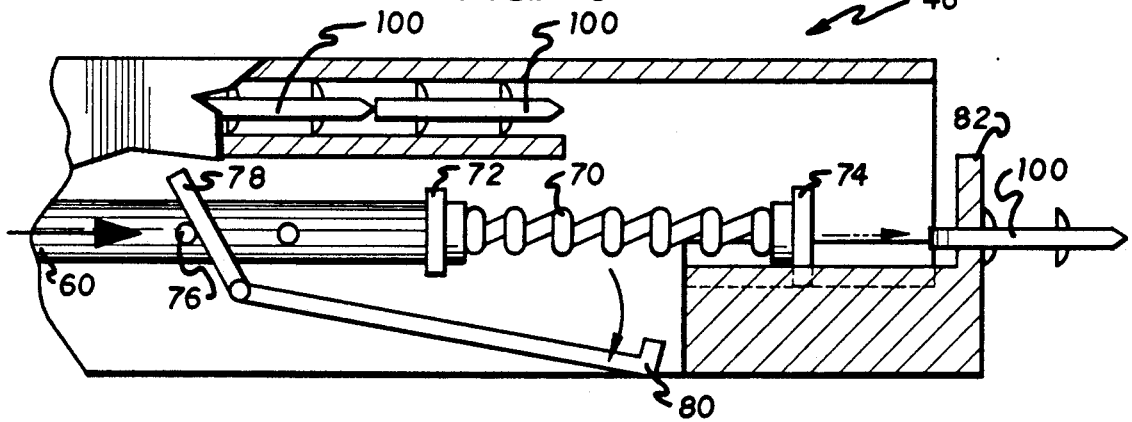
FIG. 10 is a side elevational view of the stapling mechanism showing the ejection of the staple.

FIG. 8 shows a staple 100 loaded into discharge chamber. As shown in FIG. 9, by clutching the large trigger 56, the actuation rod 60 (not shown) is advanced forward toward the stapling head 46 to compress the coil spring 70 between the compression plate 72 and the drive plate 74. Moreover, FIG. 10 shows that as the actuation rod 60 continues to advance forward, the pin 76 in communication with the actuation rod 60 engages the leverage plate 78 to pivot the retainer plate 80 downward clear of the staple 100, thus releasing the staple 100. The travel of the staple 100 is limited by the stop plate 82 which limits the penetration of the staple 100 into the pubic bone PB.

Figure 20:
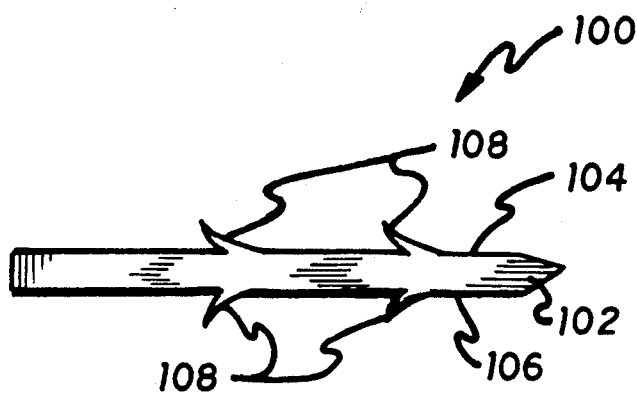
FIG. 20 is a side elevational view of the staple.

FIG. 20 shows a staple 100 for use with the stapling device 40. The staple 100 is substantially U-shaped and preferably ranges in size between 10 to 15 mm in length (to allow firm anchoring of the pelvic floor PF into the pubic bone PB) by 7 to 10 mm in width. Restricting the staple 100 to these dimensions minimizes the size of the elongated member 44 and the stapling head 46 and allows both the elongated member 44 and the stapling head 46 to be inserted into a size 10 to 11 mm trocar. If larger staples 100 are deemed necessary, the elongated member 44 and the stapling head 46 can be produced having greater dimensions (larger trocars are also available). The stock of the staples 100 is heavy enough so as to provide sufficient rigidity to permit the staple 100 to penetrate the pubic bone PB. The legs 102 of the staple 100 each have opposing surfaces 104,106, each surface 104,106 having one or more barbs or hooks 108 which expand outwardly slightly after the staple 100 has penetrated into the pubic bone PB. The slight expansion of the barbs 108 resists dislodgement of the staple 100 from the pubic bone PB.

Figure 11:
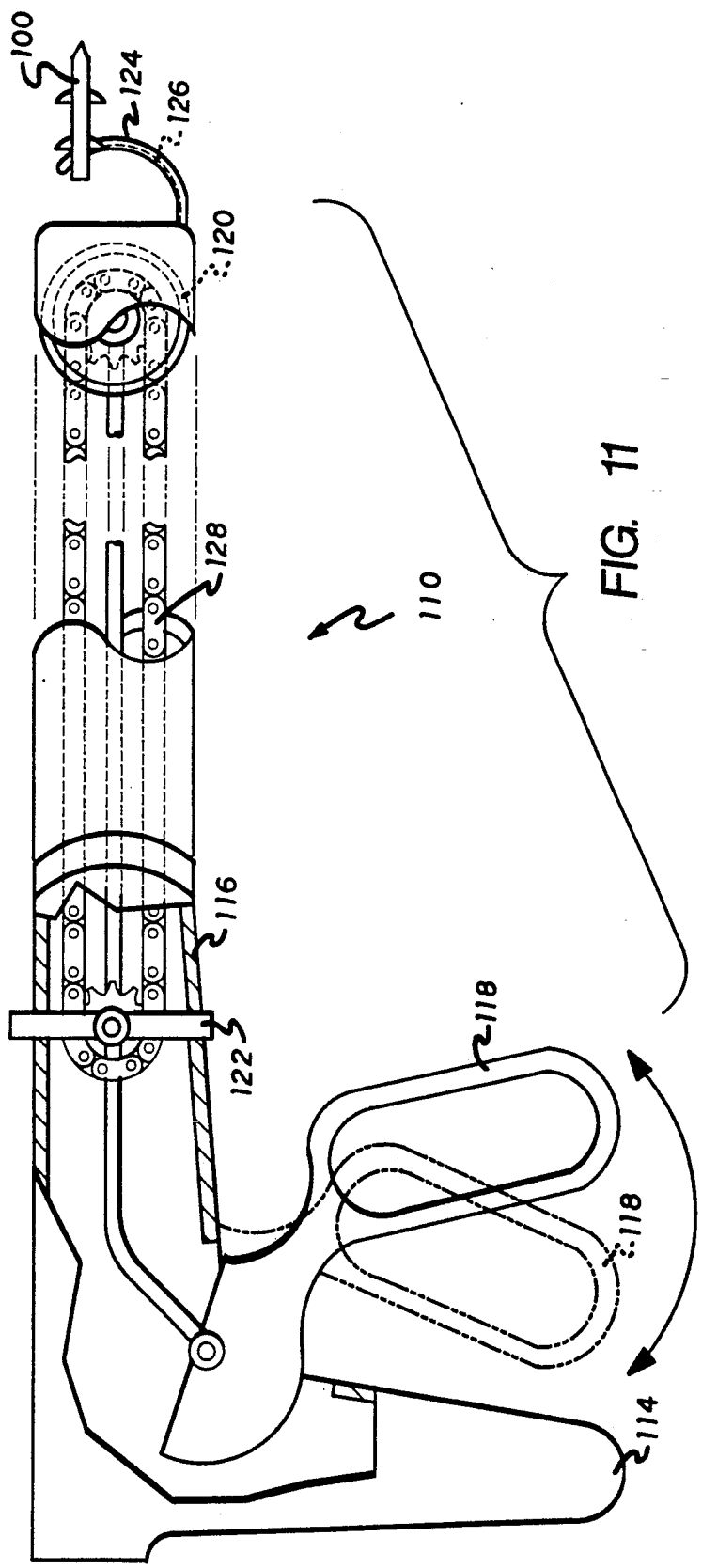
FIG. 11 is a partially broken side elevational view of the staple saw.
Figure 13:
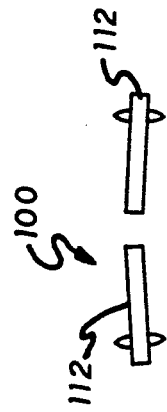
FIG. 13 is a detail view of the staple of FIG. 12 pried apart.
Figure 14:
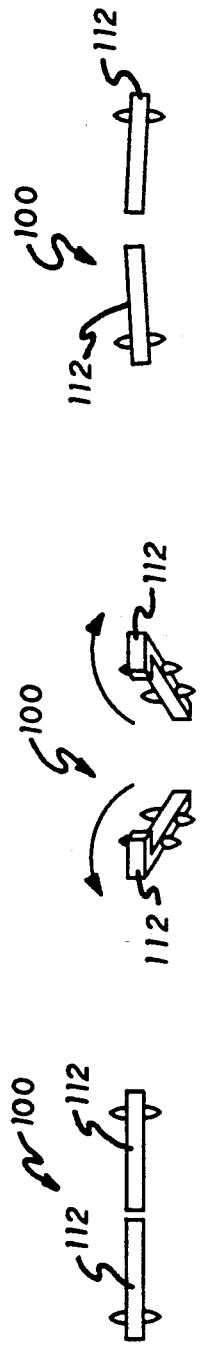
FIG. 14 is a detail view of the staple of FIG. 13 pushed back together.

In the event the pelvic floor PF is incorrectly stapled to the pubic bone PB, the barbs 108 protruding from the staples 100 will make it difficult if not impossible to remove the staple 100 from the pubic bone PB. The staple 100 would most likely need to be severed and pried open to permit the pelvic floor PF to be released therefrom. FIG. 11 shows a staple saw 110 for severing the staples 100 into two halves 112 and for prying the halves 112 apart so as to permit the pelvic floor PF to be removed from the staple 100. Similar to the stapling device 40, the staple saw 110 is comprised of a handle 114 having an elongate member 116 extending therefrom. The handle 114 is provided with a trigger 118 for advancing a saw blade 120 and a crank 122 for manually driving the saw blade 120. Opposite the handle 114, the elongated member 116 comprises a hook 124 for grappling the staple 100 to be severed. To ensure that the staple 100 is completely severed, a crevice 126 is disposed interiorly of the hook 124 to receive the saw blade 120 as the staple 100 is being cut. The saw blade 120 is driven by a chain 128 which extends from the crank 122 to the saw blade 120. Prior to cutting the staple 100, the hook 124 grapples the staple 100. While the hook 124 is grappling the staple 100, the handle 114 is compressed to advance the saw blade 120 toward the staple 100. As the saw blade 120 is advanced, the crank 122 is rotated to drive the saw blade 120 thereby severing the staple 100. After the staple 100 is cut into two halves 112 (see FIG. 13), the two halves 112 are pried apart (see FIG. 14) by the hook 124. The pelvic floor PF may now be released from the severed staple 100. Once the pelvic floor PF is released, the two halves 112 of the staple 100 are leveraged substantially back together (see FIG. 15) to reduce the risk of potential damage to the internal organs.

The laparoscopic technique is accomplished through the use of the aforementioned devices. The principle of the technique is to raise the urethra U from the position depicted in FIG. 16 to produce a greater posterior angle between the urethra U and the bladder B as shown in FIG. 17. The purpose of this technique is to permanently staple the pelvic floor (endopelvic fascia) PF to the pubic bone PB. This technique and the aforementioned devices will allow a surgeon S to see the urethra U and the lower border of the bladder B and will enable the surgeon to staple the pelvic floor PF to the pubic bone PB and to cut the staples 100 if placed incorrectly.

Figure 15:
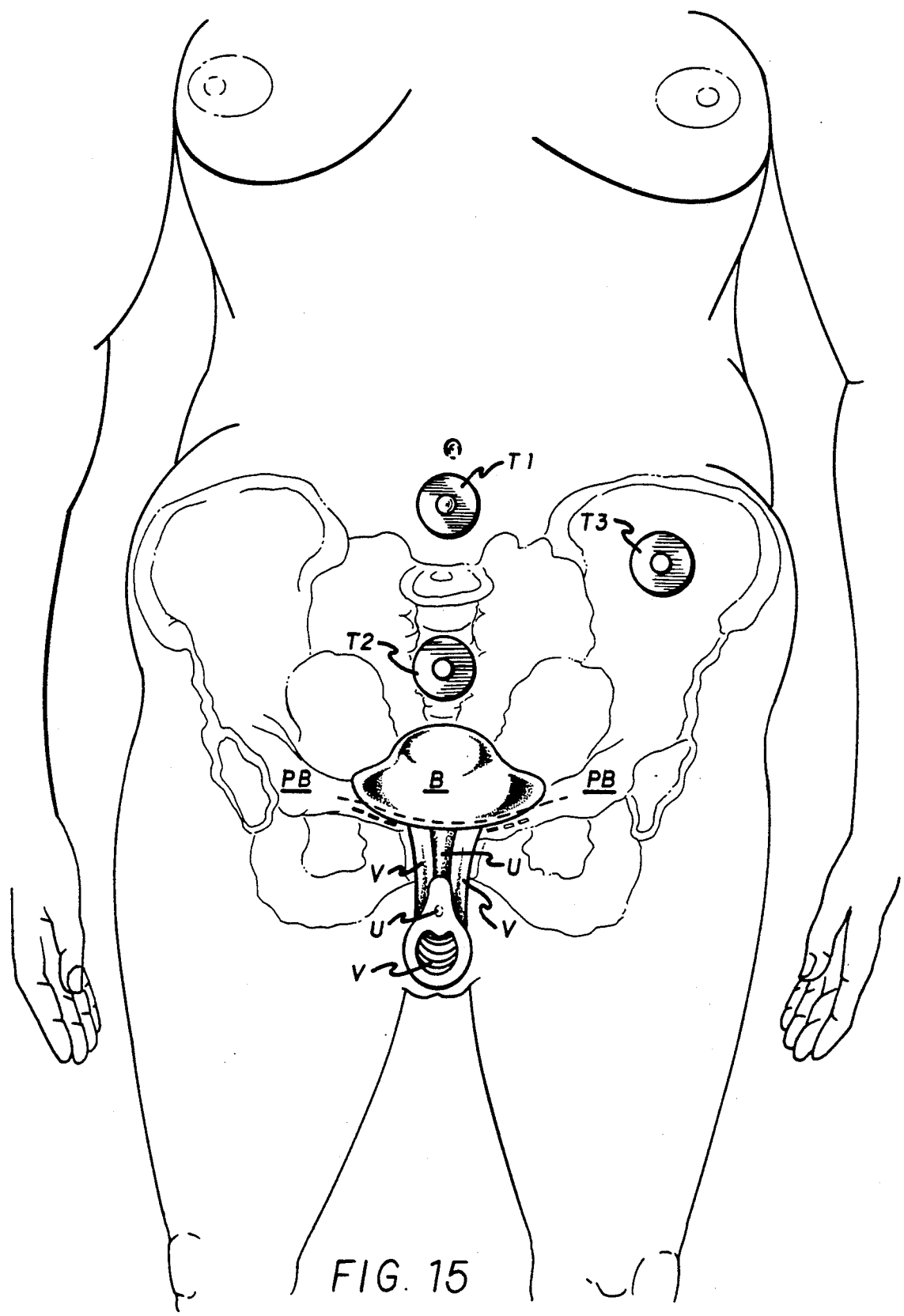
FIG. 15 is a detail view of the orientation of trocar ports relative to the anatomical structure of the patient.

As shown in FIG. 15, a trocar T1 for a video camera and one or more working trocar ports T2,T3 are applied to the abdominal cavity of the patient undergoing the surgical technique. The patient is positioned on a declined surface (not shown) with her lower body elevated above her upper body. Her abdominal cavity is inflated to create working space for the surgeon. With the patient declined and the abdominal cavity inflated by carbon dioxide, the peritoneal lining PL over the pubic bone PB and the bladder B is exposed. Once exposed, this cavity of the peritoneal lining PL is incised to allow access to the prevesical space.

Now referring to FIG. 17, the surgeon or an assistant places the fore finger F and the index finger I inside the vagina V to tent up the pelvic floor PF to a desired location for stapling. The urethral sound 10 is inserted into and through the urethra U and into the bladder B. The beads 24 on the working end of the urethral sound 10 can be seen through the wall W of the bladder B through the manual manipulation of the handle 16 (shown in FIG. 1). The beads 24 enable the surgeon to determine the location of the lower border of the bladder B, the urethra U, and the junction of the urethra U and the bladder B.

Figure 16:
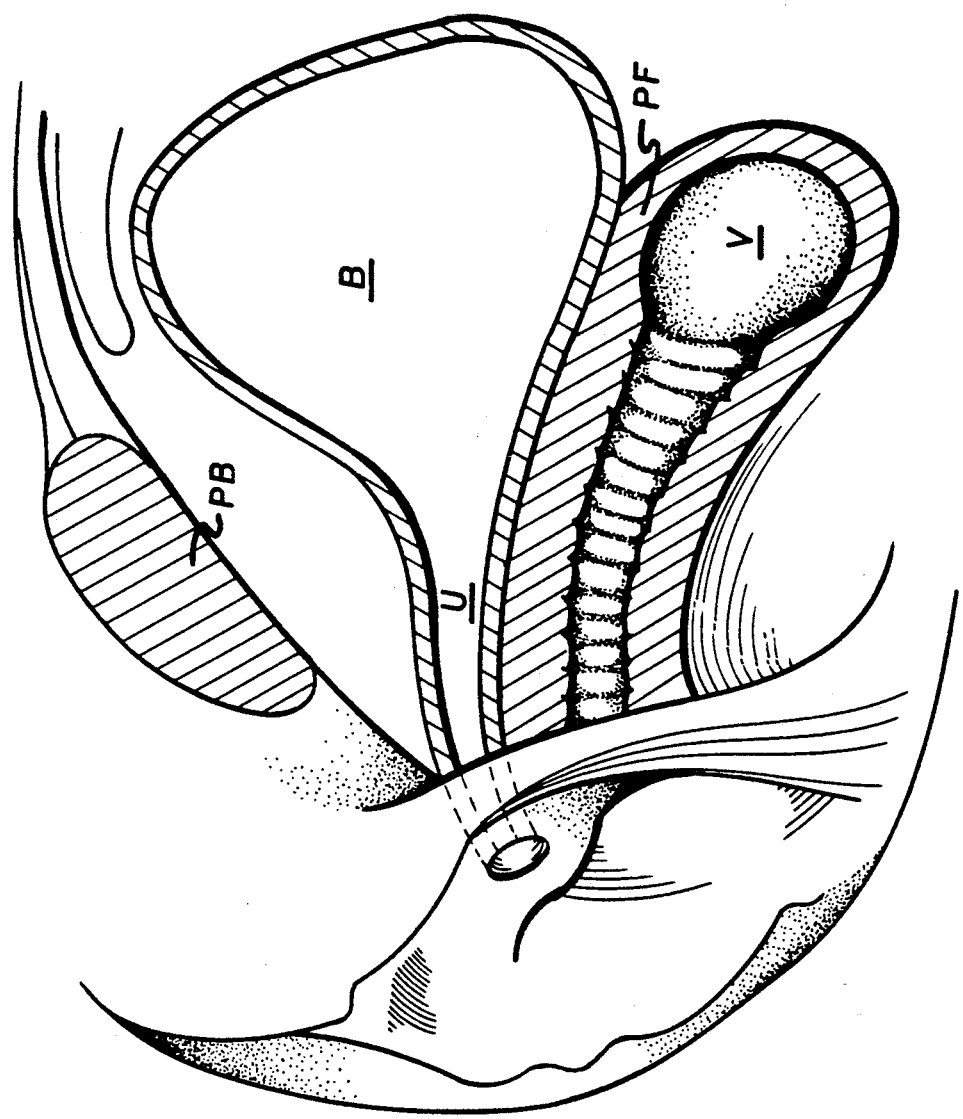
FIG. 16 is a detail view showing the orientation of the bladder prior to the performance of the laparoscopic technique.
Figure 17:
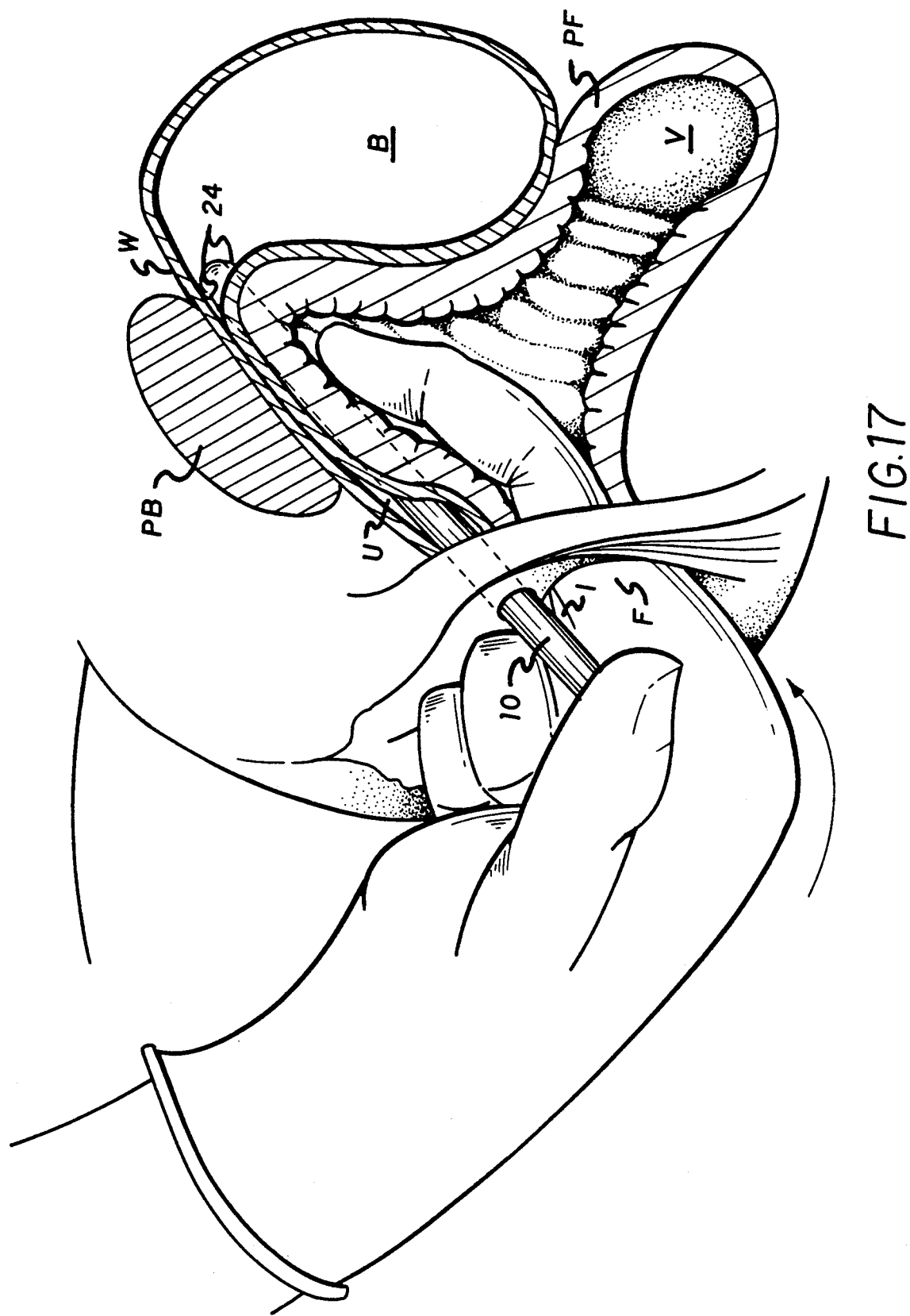
FIG. 17 is a detail view showing the urethral sound inserted into the urethra and the fore and index fingers tenting up the pelvic floor.
Figure 18:
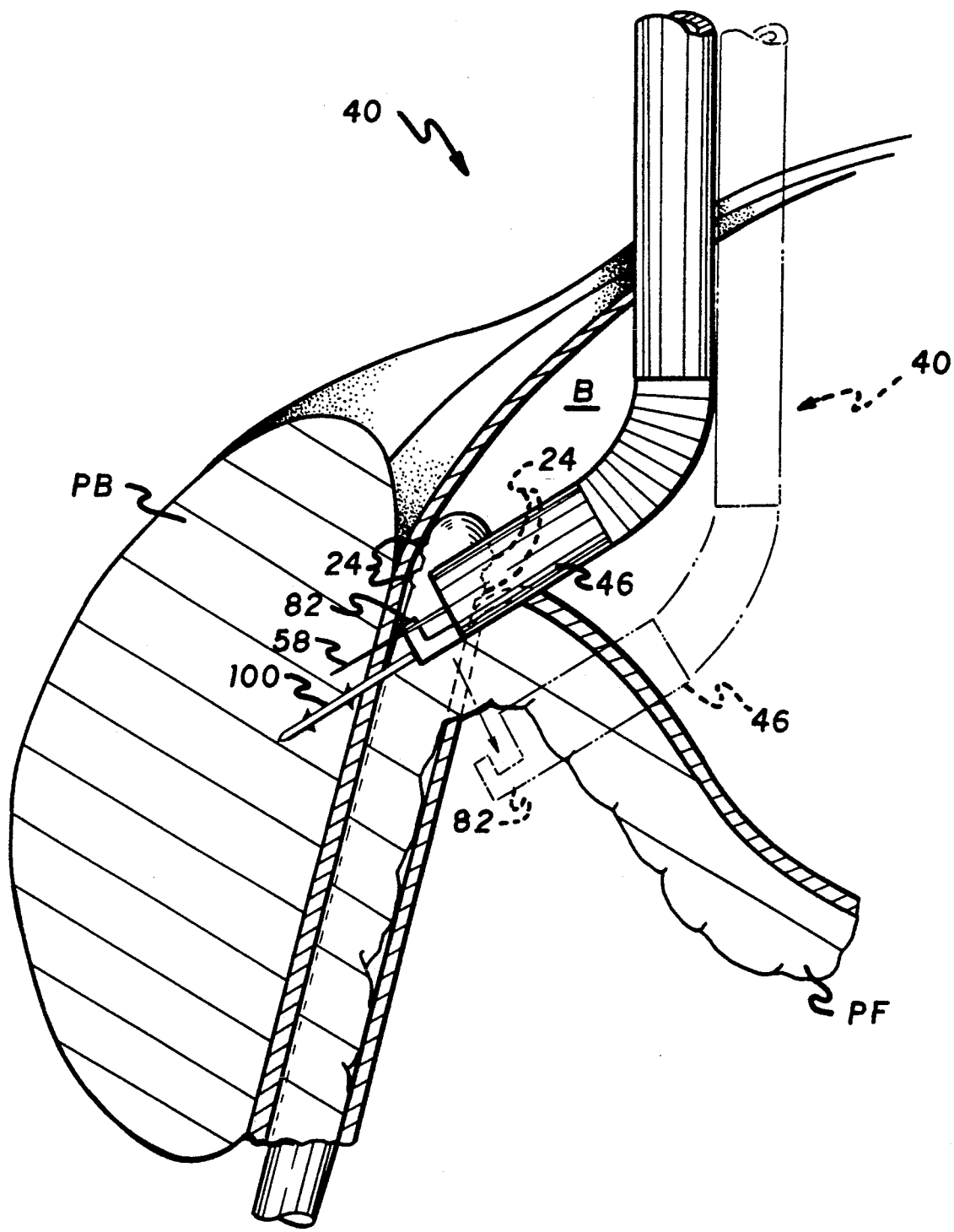
FIG. 18 is a detail view showing of the stapling device stapling the pelvic floor to the pubic bone.

With the urethral sound 10 properly positioned and the fingers F,I in the vagina V tenting up the pelvic floor (endopelvic fascia) PF to the pubic bone PB, as shown in FIG. 17, the surgeon S inserts the stapling device 40 into the trocar T2 shown in FIG. 16 and tilts the stapling head 46 at only a slight tangential angle to the elongated member 44 so as to put less downward pressure on the staple 100 and thus, reduce the risk of the staple 100 dislodging from the pubic bone PB.

The stapling device 40 is the most important device used in this surgical technique because it allows the surgeon S to staple the pelvic floor PF to the pubic bone PB at a precise location. The stapling device 40 anchors the pelvic floor PF to the pubic bone PB by advancing the target pins 58 out of the staple head 46 through the actuation of the push rod 52 (shown in FIG. 5). The target pins 58 allow the surgeon to control where the staple 100 will be located on the pelvic floor PF. It is not proper surgical technique to staple through the wall of the vagina V. This is what occurs if the surgeon gathers too much of the pelvic floor PF. With the stapling head 46 positioned properly, the stop plate 82 will rest on the pelvic floor PF pressing the pelvic floor PF against the pubic bone PB. Moreover, the stop plate 82 will limit the staples 100 depth of penetration, preventing the staple 100 from being driven completely through pelvic floor PF.

Once the surgeon S is certain that the stapling head 46 is correctly angled slightly upward with respect to the pubic bone PB at slightly less than a right angle thereby reducing the risk of the staple 100 from becoming dislodged. A staple 100 is driven into the pubic bone PB pinning the pelvic floor PF to the public bone PB. One or more staples may be placed on either side of the urethra vesical junction (the lower border of the bladder B at the junction of the bladder B and the urethra U). The stop plate 82 will stop the penetration of the staple 100 right at the pelvic floor PF, when the target pins 58 are disengaged, the stop plate 82 can slide out from behind the staple 100. The staples 100 will serve as hanging devices to properly support the weight of the pelvic floor PF. Throughout this surgical technique, the surgeon S must ascertain the lower border of the bladder B and make sure that the staple 100 does not penetrate into the cavity of the bladder B. This is accomplished by manipulating the urethral sound 10 within the bladder B.

Once the staples 100 are properly in place, the peritineus PL covering the bladder B and the pubic bone PB is reconstituted with conventional staples or sutures. A catheter is inserted into the bladder B for drainage of urine and the laparoscopic trocars T1,T2,T3 are removed accordingly.

Figure 12:
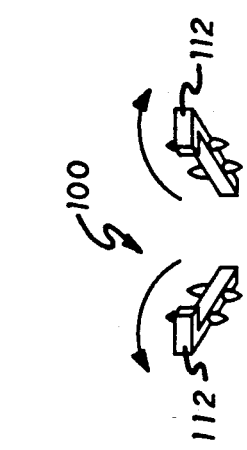
FIG. 12 is a detail view of the staple after being cut.
Figure 19:
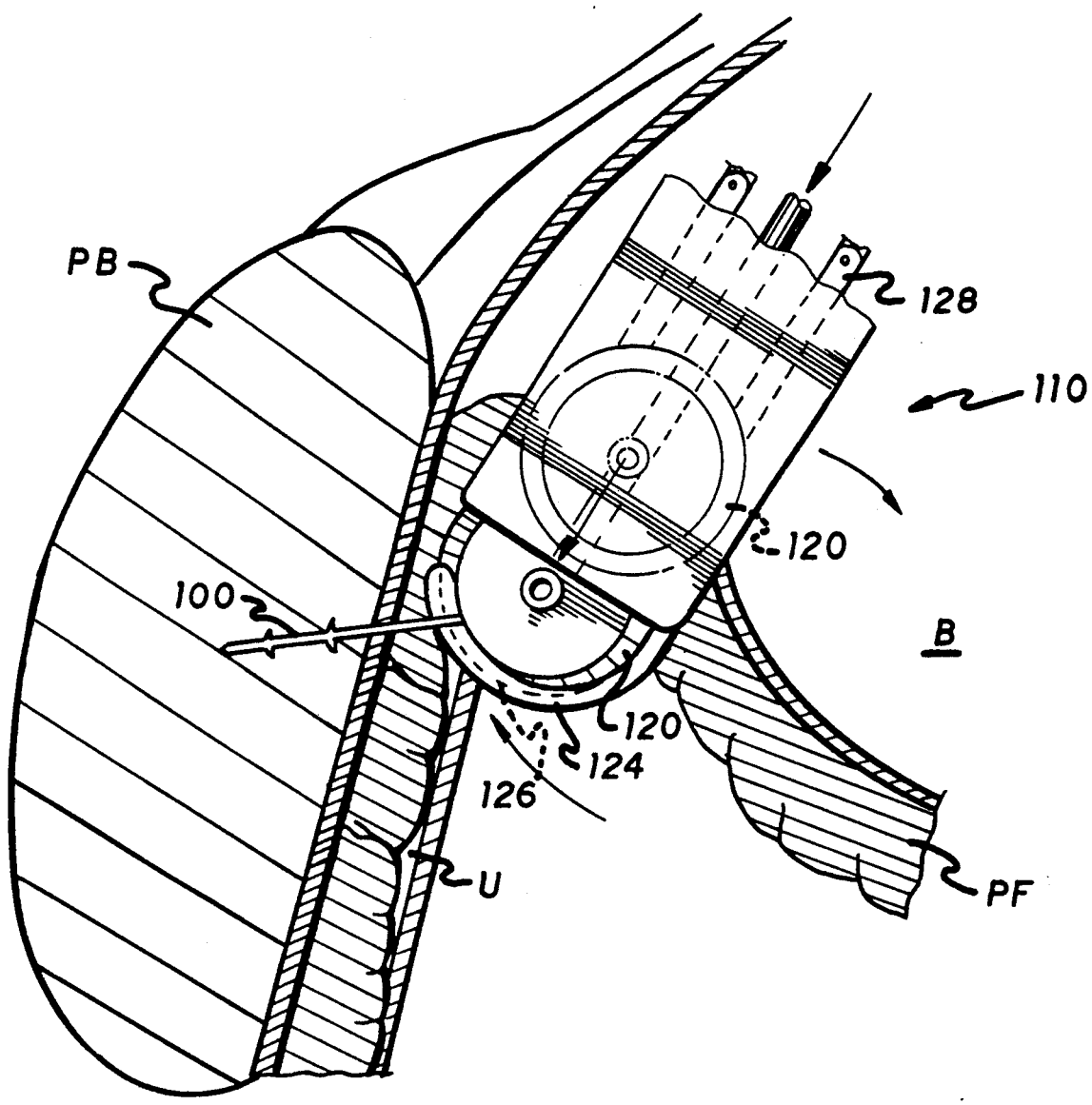
FIG. 19 is a detail view showing the staple saw severing a staple.

If the staples 100 are placed in the wrong location, they can be cut into two halves 112 by the staple saw 100 so as to release the pelvic floor PF from the staple 100 as shown in FIG. 19. The staple saw 110 has a hook 124 to engage the staple 100. The trigger 118 (shown in FIG. 11) advances the saw blade 120 against the staple 100 and the crank 122 drives the saw blade 120 via a drive chain 128 to cut the staple 100 into two halves 112 (shown in FIG. 12). Once the staple 100 is severed into two halves 112, the hook 124 is used to pry the two halves 112 (shown in FIG. 13) apart so as to release the pelvic floor PF from the staple 112. The two halves 112 are then bent back together (shown in FIG. 14) to avoid injury to the internal organs. The staples 100 are left in place because the barbs 108 on the staples 100 make it very difficult to remove the staples 100 once driven into the pubic bone PF, especially when working through a trocar T2.

It is to be understood that though the present invention was related to laparoscopic treatment, the aforementioned devices may also be used for open surgical bladder suspension in treating stress urinary incontinence. Moreover, the present invention is not limited to the sole embodiment described above, but encompasses any and all embodiments within the scope of the following claims.

I claim:

1. A surgical stapling device for stapling a pelvic floor to a pubic bone when treating female urinary incontinence, said stapling device comprising:
   a) a stapling head including:
      1) a pair of target pins for anchoring said stapling head and the pelvic floor to the pubic bone,
      2) a discharge chamber for receiving a staple to be discharged from said stapling head,
      3) a staple discharge mechanism for discharging a staple from said stapling head into said pelvic floor and further into said pubic bone;
   b) a handle including:
      1) a push rod extending through said handle for advancing said target pins forward so as to extend said target pins from said stapling head,
      2) a first, small trigger means extending from said handle for actuating a staple loading mechanism, and
      3) a second, large trigger means extending from said handle for actuating said staple discharge mechanism; and
   c) an elongated member extending from said stapling head to said handle, said elongated member providing passage for said push rod and including:
      an actuation rod for connecting said second, large trigger means to said staple discharging mechanism.

2. The stapling device according to claim 1, wherein said stapling head has a length of 3 to 4 cm to accommodate the movement of said staple discharge mechanism contained therein.

3. The stapling device according to claim 2, further comprising an aperture in said handle and means defining a plurality of notches in and along a bottom surface of said push rod, and wherein said push rod extends from said aperture in said handle, there further being a tooth disposed adjacent said aperture, said aperture being cooperatively engagable with one of a plurality of notches disposed along a bottom surface of said push rod to enable said push rod to be selectively locked into a desired position corresponding to a desired length of extension of said target pins from said stapling head.

4. The stapling device according to claim 1, wherein said elongate member has a diameter ranging from 10 to 11 mm to yield to an inside diameter of a trocar.

5. The stapling device according to claim 1, further comprising a push plate, said push rod being joined perpendicularly to one side of said push plate, an opposite side of said push plate having extending therefrom said pair of target pins.

6. The stapling device according to claim 1, further including means defining a pair of elongated bores situated on opposed sides of said stapling head, for receiving said target pins therethrough and for providing rigid radial support for said target pins.

7. The stapling device according to claim 1, further comprising a pair of coil springs, a compression plate, and a drive plate, and wherein said second, large trigger advances said actuation rod to compress said pair of coil springs, each of said coil springs being equal in length and being positioned between said compression plate and said drive plate, said coil springs each being compressible to a predetermined extent necessary to drive a staple into the pubic bone.

8. The stapling device according to claim 7, further including a leverage plate and a retainer plate, and wherein, as said actuation rod advances, said actuation rod engages said leverage plate to leverage said retainer plate to release a staple from a detained position, whereby, when a staple is released from said detained position, a staple is driven by said coil springs into the pubic bone, thus anchoring the pelvic floor thereto.

9. The stapling device according to claim 7, further including means defining a lower cavity for enabling said retainer plate to pivot downwardly to release a staple from a detained position.

10. The stapling device according to claim 7, wherein said stapling head further includes opposingly disposed channels, said compression plate and said drive plate each being slidably engagable with said opposingly disposed channels to ensure a relative axial alignment between said compression plate and said drive plate.

11. The stapling device according to claim 7, wherein each of said coil springs have two ends, one end being fixed to said compression plate and an opposite end fixed to said drive plate, said coil springs further being arranged on opposite sides of a central axis and being spaced equidistantly apart from said central axis to assure that a relative axial motion exists between said compression plate and said drive plate.

12. The stapling device according to claim 1, further including a stop plate for limiting the travel of the staple and the depth of penetration of the staple into the pubic bone.

13. The stapling device according to claim 1, further including an upper cavity for storing staples.

14. The surgical stapling device according to claim 1, further comprising, in combination, a plurality of surgical staples.

15. The surgical stapling device according to claim 1, further comprising, in combination, a plurality of surgical staples, each said staple comprising:
   a substantially U-shaped body having two legs, said legs each having opposing surfaces, each of said surfaces having a barb extending therefrom, said barbs each being slightly expandable after said staple has penetrated into a pubic bone to resist dislodgement of said staple from the pubic bone.

* * * * *